United States Patent [19]

Bankert et al.

[11] Patent Number: 5,017,472

[45] Date of Patent: May 21, 1991

[54] MICROFLOTATION DEVICES USED FOR IMMUNOASSAYS AND CELL/MOLECULAR FRACTIONATION

[76] Inventors: Richard B. Bankert, 148 Capen Blvd., Amherst, N.Y. 14226; Elizabeth A. Repasky, 66 Frankhauser Rd., Williamsville, N.Y. 14221

[21] Appl. No.: 94,520

[22] Filed: Sep. 9, 1987

[51] Int. Cl.$^5$ ................... G01N 33/53; G01N 33/543; G01N 33/537; G01N 33/531
[52] U.S. Cl. .................................. 435/7.25; 436/518; 436/519; 436/520; 436/523; 436/536; 436/538; 436/543; 436/544; 436/547; 436/808; 436/824; 436/829; 435/810; 435/7.32; 435/7.9; 435/7.92; 435/7.94; 435/975
[58] Field of Search ..................... 435/7, 810; 436/518, 436/519, 520, 523, 536, 538, 543, 544, 547, 808, 824, 829

[56] References Cited

U.S. PATENT DOCUMENTS

| | | | |
|---|---|---|---|
| 4,115,535 | 9/1978 | Giaever | 436/523 X |
| 4,342,739 | 8/1982 | Kakimi et al. | 436/518 X |
| 4,529,712 | 7/1985 | Jou et al. | |
| 4,605,630 | 8/1986 | Kung et al. | 436/829 X |

FOREIGN PATENT DOCUMENTS

| | | | |
|---|---|---|---|
| 0194156 | 9/1986 | European Pat. Off. | 436/523 |
| 8602091 | 4/1986 | World Int. Prop. O. | |

OTHER PUBLICATIONS

Ceriani, R. et al., Proc. Natl. Acad. Sci. USA, 74(2):582–586 (1977).
Mayers, G. et al., Journ. Immunol. 120(4):1143–1448 (1978).
Sharon, J. et al., Chem. Abstracts 96, Abstract No. 140899g (1982).
Mather, I. H. and Kennan, T. W. Studies on the Structure of Milk Fat Globule Membrane, J. Membrane Biol. 21:65, 1975.
McPherson et al., Reviews of the Progress of Dairy Science: The Bovine Milk Fat Globule Membrane-Its Formation, Composition, Structure and Behaviour in Milk and Dairy Products, J. Dairy Research (1983) 50:107–133.
Kobylka, D. and Carraway, K. L. Proteins and Glycoproteins of the Milk Fat Globule Membrane, Biochim. Biophys. Acta 288:282, 1972.
Huang, C.-C., Tsai, C.-M. and Canellakis, E. S. Iodination of Cell Membranes II. Characterization of HeLa Cell Membrane Surface Proteins. Biochim. Biophys. Acta. 332:59, 1973.
Anderson, M. Cawston, T. and Cheeseman, G. C. Molecular-Weight Estimates of Milk-Fat-Globule-Membrane Protein-Sodiumdodecyl Sulphate Complexes by Electrophoresis in Gradient Acrylamide Gels. Biochem. J. 139:653, 1974.
Jou, Y.-H., Mazzaferro, P. K. Mayers, G. L. and Bankert, R. B. Methods for the Attachment of Haptens and Proteins to Erythrocytes. Methods in Enzymology 92:257, 1983.

*Primary Examiner*—Robert J. Warden
*Assistant Examiner*—Jack Spiegel
*Attorney, Agent, or Firm*—Scully, Scott, Murphy & Presser

[57] ABSTRACT

This invention relates to a flotation immunoassay employing a novel buoyant matrix to which an antigen or antibody is coupled and which separates the bound and free products of the assay by floating to the surface of the reaction liquid. The novel flotation device which makes it possible to detect and to quantitate either antigen or antibody can also be used to fractionate cells and molecules.

26 Claims, 2 Drawing Sheets

ANTI-DEXTRAN COUPLED MILK FAT GLOBULES

| + RED BLOOD CELLS | + DEXTRAN COUPLED RED BLOOD CELLS | + DEXTRAN COUPLED RED BLOOD CELLS + 50 mg DEXTRAN |

A　　　　　　B　　　　　　C

MICROFLOTATION DEVICES USED FOR IMMUNOASSAYS AND CELL/MOLECULAR FRACTIONATION

FIELD OF THE INVENTION

This invention relates to novel microflotation devices for use in immunoassay and cell/molecular fractionation. More specifically, the present invention relates to the use of a novel lipid matrix which preferably is a milk fat globule (MFG), that is, a cell derivative obtained from whole milk whose plasma membrane surrounds the densely packed lipid which is responsible for its characteristic ability to float in water or buffer.

BACKGROUND OF THE INVENTION

In the past twenty years, a great deal of emphasis in the field of immunochemistry has been placed on the development of new and improved techniques for immunoassay. Immunoassay relies, in principle, on the natural reactions of the body's immune system to the presence of foreign substances introduced into the body. The immune system is provoked by these foreign materials, for example, infectious organisms such as bacteria or viruses, to produce antibodies which react specifically with the foreign substance (or antigen) and which, if effective, aid in the elimination of the organisms from the body. The production of antibodies, of course, is not limited to the presence of infectious microorganisms but is also observed in response to many materials which are not normally found in circulation in the body.

The use of immunoassay techniques for diagnostic testing, that is detection of antigen or antibody, has recently become very widespread and now is so frequently employed in both research and clinical environments that it may be considered commonplace.

The relative specificity of antibody for a particular antigen has provided the basis for highly specific and accurate diagnostic testing for various physiological conditions such as infectious diseases, pregnancy and presence of drugs in the body. In practice, the test operates by exposing a test sample suspected of containing a particular antigen such as a bacterium or antibody to a particular microorganism such as the AIDS virus to a detectably labelled corresponding "immunological partner," i.e., the complementary antibody or antigen. The specificity of the antigen-antibody reaction is thus exploited in such well-known immunodiagnostic techniques as precipitation reactions, immunodiffusion, agglutination or hemolysis of antigen coated red cells, bacteria or latex particles, complement fixation, fluorescent immunoassays, immunoelectrophoresis, radioimmunoassay (RIA), and enzyme immunoassay (EIA), including enzyme-linked immunosorbent assay (ELISA). Two techniques of immunoassay, RIA and EIA, have become particularly popular because of their generally superior sensitivity, and the greater safety involved in EIA.

Many of these assays are sensitive and specific, but all are limited by one or more of the following: requirements of expensive laboratory equipment (e.g. gamma counter, fluorescence microscope, high speed centrifuge, spectrophotometer, etc.), a technician trained in the operation of these instruments, and reagents which present some hazard or require refrigeration. In addition, some of the assays are relatively insensitive, not quantitative and require several hours or even days to complete.

It would be highly desirable, therefore, to provide a cost effective, simple and sensitive diagnostic immunoassay which can provide an unequivocal positive and negative end point within a matter of minutes, which assay can be used quantitatively as well as qualitatively, that requires minimal laboratory equipment and that the components of the assay can be made shelf stable easily.

BRIEF SUMMARY OF THE INVENTION

The present invention provides a novel diagnostic immunoassay having the foregoing advantages which involves the use of a buoyant matrix which readily separates the bound and free products of the assay by floating to the surface of the reaction fluid. Specifically, the preferred matrix for use in the present invention is composed of milk fat globules (MFG) which comprise the cream fraction of milk and consist of fat droplets which are stabilized by an external membrane derived mainly from the apical plasma membrane of mammary secretory cells. The milk fat globule thus provides a natural, abundant and inexpensive microflotation device with the desired characteristics that readily permits the coupling of antigens or antibodies.

The novel flotation immunoassay of the present invention, therefore, offers several advantages over existing assays. The present flotation assay generates an end point within minutes which is simple to read and requires no laboratory equipment or at most a simple clinical centrifuge. Secondly, the raw materials for the assay are extremely inexpensive, can be stabilized by glutaraldehyde and have no biohazardous elements, such as radioactivity. Thirdly, the use of the present flotation immunoassay makes it possible to design assays that are homogeneous, i.e. they require no separation techniques such as centrifugation or washing of antigen-antibody pellets.

In addition, the flotation concept of the present invention provides a means for the separation of heterogeneous mixtures of cells or molecules. In this approach, the requirements are that MFG be coupled with an antigen or antibody, which reacts with the surface of the cell to be separated or with the molecule to be separated.

The novel flotation immunoassay can be applied to a wide range of clinically relevant molecules including drugs, pathogenic bacteria, fungi, viruses, cellular antigens, such as blood group antigens and leukocyte antigens and tumor specific antigens. The only requirements are that the antigen or the antigen-specific antibodies are able to be linked to the buoyant matrix and the indicator.

DETAILED DESCRIPTION OF THE INVENTION

Figure 1:
Figure 1:
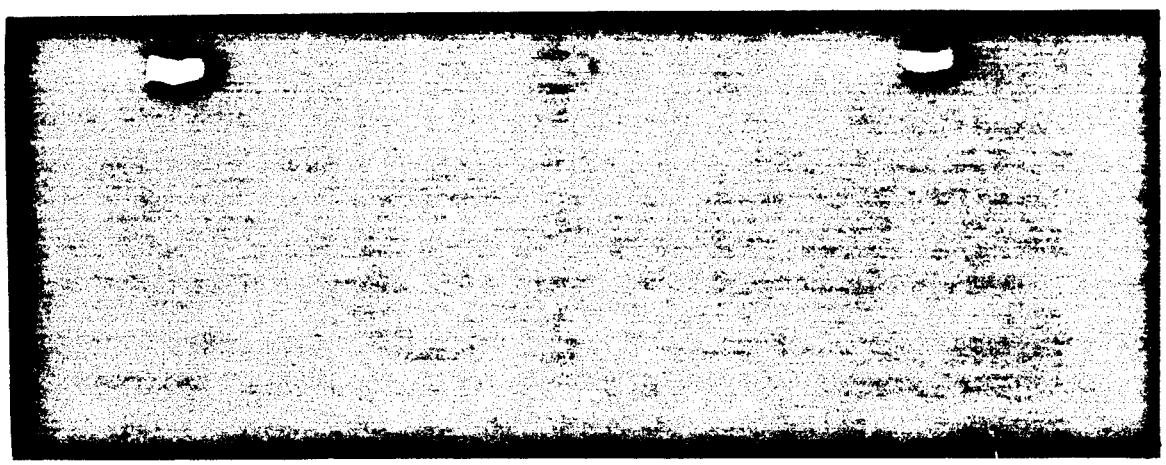

The present invention is based upon the discovery that it is possible to provide a highly useful flotation assay which floats in water or buffer and can serve as a matrix for covalent attachment of antigens or antibodies. Milk fat globule (MFG), which is our preferred matrix, provides a natural, abundant and inexpensive flotation device with the desired characteristics.

As stated earlier, milk fat globules (MFG) comprise the cream fraction of milk and consist of fat droplets that are stabilized by an external membrane derived mainly from the apical plasma membrane of mammary secretory cells. Keenan, et al. *J. Dairy Science,* 54:295, 1971. As such, these milk fat globules consist of a triglyceride core surrounded by a lipid bilayer containing integral membrane proteins. Mather and Keenan, *J. Membrane Biol.* 21:65, 1975. The globules range in size from 1 to 10 μm diameter surrounded by a thin membrane called the milk fat globule membrane (MFGM). This membrane (approximately 10 nm in cross-section) consists of a complex mixture of proteins, phospholipids, glycoproteins, triglycerides, cholesterol, enzymes and other minor components. McPherson, et al. *J. Dairy Research* (1983) 50:107–133. Studies of the membrane proteins have revealed that several of these are glycoproteins and that the proteins are asymmetrically arranged in the membrane such that portions of them are exposed on the external surface of the MFG. Kobylka, et al. *Biochim. Biophys. Acta* 288:282, 1972, Huang, et al. *Biochim. Biophys. Acta* 332:59, 1973 and Anderson, et al. *Biochem. J.* 139:653, 1974.

The milk fat globules consist of 99% triglycerides which are synthesized in the mammary gland secretory cell from precursors in the blood (i.e. glucose, acetate, low density serum lipoproteins) This high lipid content gives the globules a density less than that of water so that they float to the top of an aqueous suspension. MFG can thus be readily isolated by simply allowing them to rise to the top of a suspension upon standing, or by centrifugation at low speed in a clinical centrifuge, or for large scale preparations, by separating in a mechanical cream separator.

We have found that the stability of the MFG is improved by immediate washing of fresh milk in PBS, by storage at room temperature and by gentle fixation by dialysis against 1% glutaraldehyde. We have also found that the MFG is unaffected by the tonicity of the solution to which it is exposed, in that exposure to hypotonic or hypertonic solutions has no visible effect on the MFG.

In the flotation immunoassay of the present invention, the antigen or antibody is covalently coupled to the glycoproteins of the MFG by a variety of chemical techniques as, for example, the techniques described by Jou, et al. in *Methods in Enzymology*, Vol. 92: 257 (1983), which is incorporated herein by reference.

As therein described the coupling of proteins and haptens to erythrocytes, for example, involves the use of a heterobifunctional reagent, e.g. N-succinimidyl 3-(2-pyridyldithio)propionate to link proteins to sheep red blood cells (SRBC) through disulfide bond formation. A second method takes advantage of succinylation of hapten-protein conjugates to facilitate the coupling to the surface of SRBC by carbodiimide. These two methods are designed to couple haptens to the surface of SRBC by using another heterobifunctional reagent, methyl-p-hydroxybenzimidate or a multifunctional reagent, 1,3,5-trichlorotriazine. A third method employs the noncovalent attachment of proteins and aminohaptens to the surface of SRBC via a synthetic lipopolysaccharide reagent.

This latter method attaches the antigen to the surface of a cell without a covalent bond to the membrane molecules. A lipopolysaccharide, myristol-oxidized dextran, (MOD) has been designed to which haptens and proteins can be covalently coupled. The antigen-MOD directly attaches to the surface of the cells via a stable hydrophobic interaction with the plasma membrane. It is believed that the antigen-MOD is attached to the surface of red blood cells via the intercalation of the lipid moiety of the lipopoly-saccharide into the hydrophobic portion of the plasma membrane. The covalent attachment of haptens and proteins to the MOD occurs between free amino groups present on the haptens or proteins and reactive aldehyde groups on the MOD. The synthetic lipopolysaccharide can be used as a general method for coupling haptens or proteins to red blood cells.

Thus, we have been able to couple antibodies to MFG indirectly by first linking the antibody to oxidized dextran after coupling dextran to myristoyl chloride. The myristic acid moiety intercalates into the MFG membrane and the bound antibody can be detected on the surface by agglutination of the MFG by antigen or anti-Ig antisera.

We have also been able to couple N-hydroxy-succinimide biotin to the MFG surface and to detect this coupling by fluorescence microscopy after adding fluorescently labelled avidin.

Similarly, dextran has been coupled to red blood cells, MFG, bacteria (*E. coli* and *B. subtilis*) and horseradish peroxidase by first oxidizing the dextran using sodium periodate followed by the formation of a Schiff base with amino groups on the cells or HRP. The reaction products are then stabilized with sodium borohydride.

As stated earlier, the antigen or antibody is coupled to the glycoproteins of the MFG by using one of the three methods heretofore described. Complementary antibody or antigen is attached to the surface of a colored indicator such as erythrocytes, which would provide a red color, stained bacteria or some other readily visible indicator. An indicator visible to the naked eye is preferred. Interaction between the complementary ligands of the MFG and the indicator create a complex which rises to the top of the reaction mixture in a test tube, for example, by virtue of the flotation property of the MFG.

When such an interaction has occurred, the presence of the colored indicator with the MFG at the top of the reaction tube can be seen (e.g. red blood cells, stained bacteria, enzyme). In the absence of reaction between the MFG and an indicator no color will be seen in the MFG layer, but rather when cells have been used as indicator, these are seen as a residue at the bottom of the tube. This standard assay can be modified in a variety of ways to perform quantitative analyses and to analyze the presence of antigen (Ag) or antibody (Ab) in a test sample by inhibition of the flotation of the indicator.

Thus, when Ag coated MFG are reactively contacted with a suspension of antibody-conjugated red blood cells (Ab-RBC) in buffer, the Ab-RBC bind to the MFG and rise to the top of the reaction vessel forming a red ring at the surface. When assaying for the presence of the antibody the test sample is first reactively contacted with the Ag-coated MFG. If the sample contains antibody, it will bind to the Ag on the MFG and thereby inhibit the binding of the Ab-RBC when the indicator system is added subsequently. The MFG again rises to the top but in the absence of bound Ab-RBC the color of the ring at the top of the reaction vessel is white and the Ab-RBC fall to the bottom of the tube if not bound to the MFG.

The operation of the hereinafter described flotation immunoassay is schematically shown below:

| | Anticipated Outcome |
|---|---|
| A. Assay for Presence of Antibody | |
| (1) Ag-MFG + Test Sample (Ab) | In the presence of antibody the complex formed between Ag-MFG and Ab from test sample rises to top of reaction vessel forming a white ring, and the unbound indicators (Ab-RBC) form a red spot on bottom of reaction vessel. |
| (2) Ab-RBC (added subsequently) | |
| OR | |
| (1) Ag-MFG + Test Sample (No Ab) | In absence of Ab in test sample, the complex formed between Ag-MFG and Ab-RBC rises to top of reaction vessel forming a red ring. |
| (2) Ab-RBC (added subsequently) | |
| B. Assay for Presence of Antigen | |
| (1) Ab-MFG + Test Sample (Ag) | In the presence of antigen the complex formed between Ab-MFG and Ag from test sample rises to top of reaction vessel forming a white ring and the unbound indicators (Ag-RBC) form a red spot on bottom of reaction vessel. |
| (2) Ag-RBC (added subsequently) | |
| OR | |
| (1) Ab-MFG + Test Sample (No Ag) | In absence of Ag in test sample, the complex formed between Ab-MFG and Ag-RBC rises to top of reaction vessel forming a red ring. |
| (2) Ag-RBC (added subsequently) | |
| C. Assay for Antibody | |
| (1) Ag-MFG + Ag-RBC + Test Sample (Ab) (present simultaneously) | In the presence of Ab in the test sample a bridge complex formed between MFG-Ag:Ab:Ag-RBC rises to the top of the reaction vessel forming a red ring. |
| OR | |
| (1) Ag-MFG + Ag-RBC + Test Sample (No Ab) (present simultaneously) | In the absence of Ab in test sample, unbound Ag-MFG forms a white ring at the top of the reaction vessel and unbound Ag-RBC forms a red spot on the bottom. |
| D. Assay for Antigen | |
| (1) Ab-MFG + Ab-RBC + Test Sample (Ag) (present simultaneously) | In the presence of antigen in the test sample a bridge complex formed between MFG-Ab:Ag:Ab-RBC rises to the top of the reaction vessel forming a red ring. |
| OR | |
| (1) Ab-MFG + Ab-RBC + Test Sample (No Ag) (present simultaneously) | In the absence of Ag in test sample, unbound Ab-MFG forms a white ring at the top of the reaction vessel and unbound Ab-RBC forms a red spot on the bottom. |

In the examples hereinafter a well defined system of pure antigen and monoclonal antibody are shown. The antigen used is a dextran derived from the bacterium *Leuconostoc mesenteroides*. This antigen is a well-characterized molecule consisting primarily of α-1,3 and α-1,6 sugar linkages. Its high molecular weight and physicochemical characteristics combine to make this molecule highly immunogenic and easy to couple to the surface glycoproteins of either MFG or to the indicator system. This molecule is easily purified Finally this antigen is present in the cell wall of several bacteria and is associated with Aspergillus. The antibodies are monoclonal antibodies specific for the α-1,3 linkage groups of the dextran.

In addition to the novel flotation immunoassay described above, we have also found that MFG can be used to fractionate cells and molecules. This is demonstrated by the fact that sheep red blood cells (SRBC) to which dextran has been covalently linked bind to MFG which have on their surface anti-dextran or dextran In the latter case anti-dextran is added to link dex-MFG and dex-SRBC.

The invention will be described in greater detail in conjunction with the following specific examples which demonstrate the feasibility of the hereinabove described flotation immunoassay.

EXAMPLE A

Assay for the Presence of Antibody

Dextran to be coupled to milk fat globules is first oxidized by treating a solution of dextran at a concentration of 10 mg/ml in phosphate buffered saline, pH 7.4 (PBS) with sodium periodate at a final concentration of 10 mM for one hour at room temperature. The oxidized dextran is subjected to extensive dialysis against 100 volumes PBS at 40° C. The milk fat globules are obtained from raw bovine milk by centrifugation at 1500×g for 10 min at room temperature followed by removal of the underlying (sub-natant) aqueous material. The milk fat globules are washed three times by the addition of PBS to the original volume followed by centrifugation at 1500×g for 10 min and removal of the sub-natant fluid To 0.9 ml packed MFG is added 0.1 ml oxidized dextran and the mixture is incubated overnight at room temperature. The oxidized dextran binds to amino groups on the surface of the MFG forming a Schiff base. The resulting dextran coupled milk fat globules are transferred to a 10 ml syringe fitted with a stopcock, brought to 10 ml with PBS and centrifuged at 1500×g for 10 min. The sub-natant fluid is removed by opening the stopcock and the milk fat globule layer is washed three times by gentle suspension in 10 ml PBS followed by centrifugation. The final milk fat globule layer is brought to a final concentration of 20 percent (v/v) by the addition of approximately 4 ml PBS for storage at room temperature.

The Schiff base so formed between oxidized dextran and the MFG can be stabilized by the addition of 10 mM sodium borohydride prior to washing of the dex-MFG. The reduced dex-MFG can be stabilized further by dialysis overnight against 100 volumes of a solution of 1 percent glutaraldehyde in PBS. Partial sterilization of the dex-MFG can be obtained by treatment with 10,000 rads of gamma irradiation without loss of the flotation properties or of the antigenicity of the dextran.

The efficiency of coupling can be assessed by incubating dex-MFG with anti-dextran antibodies and microscopically observing agglutination of the dex-MFG.

The antibodies, to be coupled to the indicator red blood cells, are treated with the heterobifunctional reagent, N-succinimydyl-3-(2-pyridyldithio)propionate (SPDP). Modification of the antibody is achieved by incubating with SPDP at room temperature with stirring at a molar ratio of 25 to 1:100. This yields approximately 5-20 pyridyldithiopropionate (PDTP) molecules per antibody molecule, assuming an efficiency of coupling of 20 percent. The required ratio is derived empirically for each protein. In the case of the MOPC 104E monoclonal anti-dextran antibody used here, a ratio of 1:100 is used. Extensive dialysis of the resultant modified antibodies is performed against 1,000 volumes of PBS at 4° C.

The red blood cells (RBC) to which antibody is to be coupled are obtained by venous puncture of sheep, are defibrinated and washed three times and stored as a 50 percent (v/v) suspension in PBS. Prior to treatment with PDTP modified antibody, 12.5 ml of a 2 percent suspension of RBC in PBS are incubated with 0.5 ml of freshly prepared 1M dithiothreitol (DTT) for 1 hour at room temperature in order to reduce disulfide groups on the cell surface to thiol groups. Free DTT is then removed by washing the reduced RBC four times by the addition of 15 ml PBS, centrifugation at 1,500×g for 10 min and removal of the supernatant fluid. To the resultant 0.25 ml packed reduced RBC is added 0.5 ml PDTP modified anti-dextran antibodies, and the mixture incubated on a rotating shaker overnight at room temperature. The resultant anti-dex-RBC are washed four times by the addition of 15 ml of PBS, centrifugation at 1,500×g for 10 min and removal of the supernatant fluid. The final RBC pellet is brought to a final concentration of 10 percent (v/v) by the addition of approximately 2.25 ml PBS for storage at 4° C.

The anti-dex RBC can be stabilized, as above, using 1 percent glutaraldehyde and sterilized, as above.

The efficiency of coupling can be assessed by incubating anti-dex-RBC with an antibody prepared against the MOPC 104E protein and microscopically observing agglutination of the anti-dex-RBC.

The addition in a 6×60 mM tube of 50 μl of a 2% (v/v) suspension of the thus-prepared anti-dex-RBC to 250 μl of a 4% (v/v) dex-MFG suspension in a total volume of 500 μl followed by gentle mixing and incubation at room temperature for 30-60 minutes results in a strongly positive "red ring" at the top of the tube. When control RBCs (i.e. no dextran on the surface) are added, the red color (i.e. the hemoglobin associated with the RBC) appears at the bottom of the reaction tube.

The addition of a test sample containing antidextran antibodies results in the antibody binding to the dex-MFG and inhibits the binding of the indicator-RBC to the milk fat globules, that is to say, in the presence of anti-dextran antibodies the MFG ring at the top of the reaction tube is white and all of the indicator cells fall to the bottom of the reaction tube. This demonstrates the specificity of the immunoassay and it demonstrates the ability of the immunoassay to detect the antibody (antidextran) in a test sample.

EXAMPLE B

Assay for the Presence of Antigen

Antibody is covalently coupled to the surface of MFG following the procedure of Example A. The complementary antigen, dextran, is coupled to the indicator RBC by the procedure in Example A. When the reaction is performed as in Example A, and antigen is present in the test sample it binds to the antibody MFG and inhibits the binding of the indicator, dex-RBC. Accordingly, the dex-RBCs fall to the bottom of the reaction vessel (test tube) forming a red spot and the Ab-MFG rises to the top forming a white ring. See C of the photograph shown in FIG. 1 of the annexed drawing. When no antigen is present in the test sample, the indicator dex-RBCs bind to the MFG and rise to the top of the reaction vessel forming a positive red ring. See B of the photograph shown in FIG. 1 of the annexed drawing. When control RBCs are used (with no dextran on the cell surface) the indicator cells fail to bind to the Ab-MFG and fall to the bottom of the tube forming a red pellet at the bottom of the tube and a white ring of Ab-MFG at the top. See A of the photograph shown in FIG. 1 of the annexed drawing.

EXAMPLE C

Assay for the Presence of Antibody

Milk fat globules (MFG) coupled to dextran (dex-MFG) following the procedure outlined in Example A and red blood cells (RBC) coupled to dextran (dex-RBC) following the procedure of Example A, are mixed in a 1:1 ratio in a reaction vessel in the presence of a monoclonal anti-dextran antibody. Microscopic observation reveals clumps of mixed dex-RBC and dex-MFG. When this experiment is carried out in a 6×60 mm tube in a total volume of 500 ul containing equal volumes of 2% dextran-MFG and 1% dextran-RBC, the indicator red cells bind to the MFG and rise to the top of the tube forming a red ring. No RBCs are present in the MFG layer in the absence of added antibody or when either the MFG or RBC used in the assay have no dextran coupled to them. Thus the indicator cells that are bound to the MFG rise to the top of the tube immediately after a low speed spin in a clinical centrifuge (500×g) and can be readily visualized grossly. The same result occurs when the reaction tubes are allowed to settle without centrifugation.

EXAMPLE D

Assay for Presence of Antigen

Antibody is covalently coupled to both MFG and indicator SRBC following the procedure of Example A. When the antigen is present in the test sample it forms a bridge between the Ab-MFG and the Ab-SRBC so that the indicator red cells rise to the top of the test tube forming a red ring. In the absence of antigen in the test sample, no red cells bind to the MFG and the ring at the top of the assay tube is white, that is, only the MFG is present.

While the invention has been described hereinabove particularly with regard to milk fat globules as the lipid source and red blood cells as the indicator, it is within the scope of the present invention to employ other materials in the described immunoassay. Thus, we may substitute stained bacteria, e.g. *E. coli* and *B. subtilis*, horseradish peroxidase, etc. for the indicator red blood cells.

It is expected that phospholipid formulations can be used to prepare lipid vesicles with densities less than water to replace MFGs as the buoyant matrix. It is also possible to use synthetic polymers to prepare tiny spheres or beads with chemically reactive groups on their surface for the attachment of antibodies or antigens.

It is also within the scope of the present invention to use many different antigens and polyclonal antisera or monoclonal antibodies directed against them. Among the antigens which can be used are: 1) macromolecular antigens, including proteins, carbohydrates and nucleic acids, 2) haptens, such as N-ε-dinitrophenyl-lysine, 3-aminopyridine, 4-aminopyridine, 4-aminophthalate and 5-aminoisophthalate, 3) antigens associated with microbial cells, both pathogenic and non-pathogenic, including bacteria (e.g. Pseudomonas, Mycobacterium), fungi (e.g. Candida) viruses (e.g. AIDS virus, retroviruses), and protozoa (e.g. Schistosoma), 4) cell surface antigens, such as blood group antigens, specific T cell antigens (e.g. Thy-1, lyt2, L3T4, T4, T8, etc.), 5) tumor specific antigens, e.g. the 160,000 molecular weight glycoprotein (gp160), a cell surface molecule associated with human lung tumor cells. Many of these molecules have been or can readily be coupled to RBC and/or MFG using the techniques outlined above and described in Jou et al., *Methods in Enzymology* 92: 257–275 (1983). For example, in addition to coupling dextran as described, the above-mentioned haptens have been successfully conjugated to membrane using myristoyl-oxidized dextran as the coupling agent. Proteins that have been successfully coupled, in addition to the monoclonal anti-dextran antibodies, include Bence-Jones protein, human γ-globulin, bovine γ-globulin, rabbit anti-human Fab antibody, mouse anti-phthalate antibodies and monoclonal anti-phthalate antibody.

Figure 2:
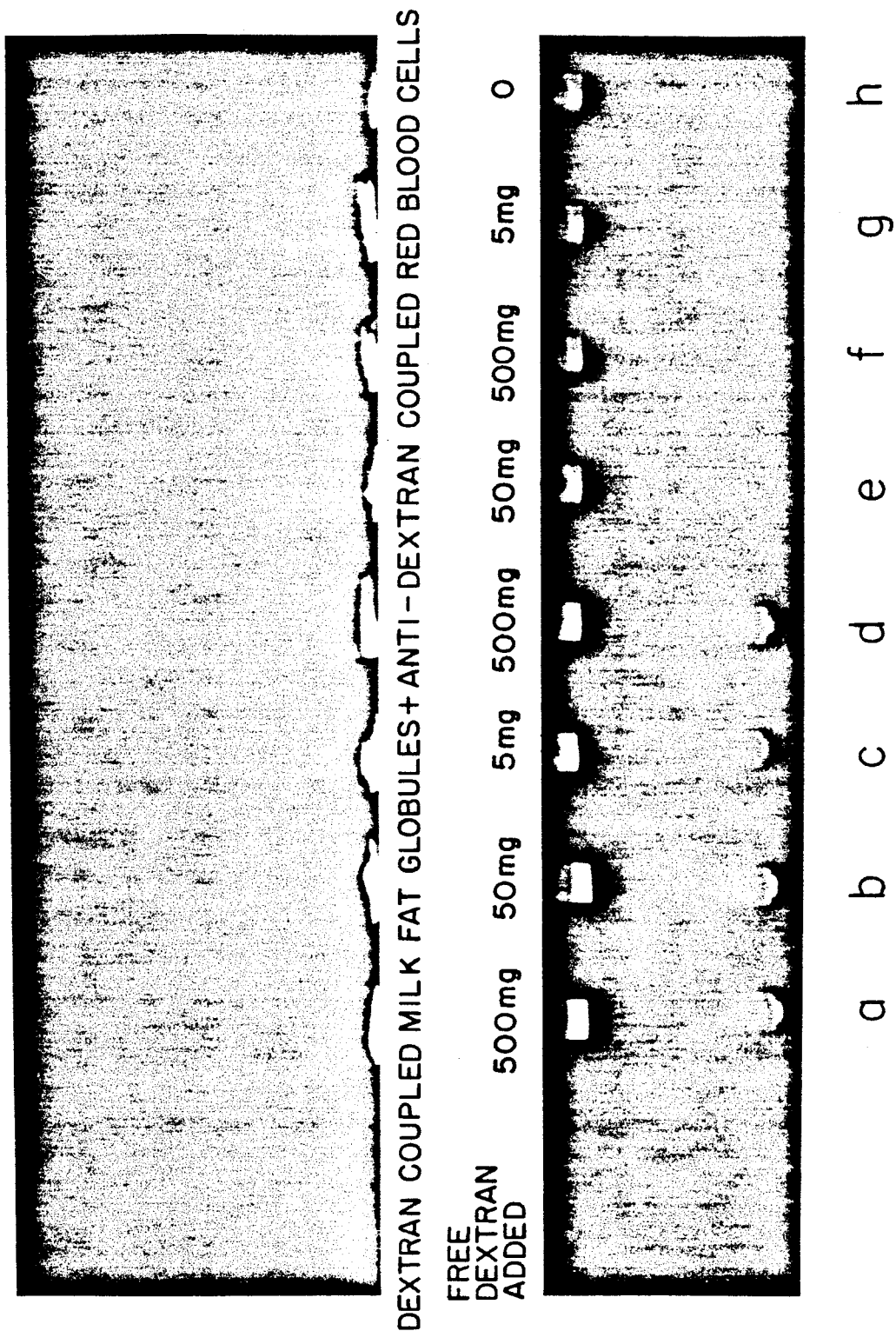

The invention as described herein can also be used in a quantitative fashion, although the examples given have for clarity been described for the qualitative determination of the presence or absence of antigen or antibody. For a quantitative assay, standard samples containing a known amount of antigen or antibody can be diluted serially two-fold and incubated with the appropriately coupled MFG and indicator RBC. In this way, it is possible to determine the end-point, i.e. the smallest amount of antigen or antibody capable of inhibiting binding of the indicator RBCs to MFGs and thus preventing the appearance of red color at the top of the tube. Similar dilution of the test sample containing unknown quantity of antigen or antibody to an end point would allow the calculation of the amount of antigen or antibody in the test sample. One example which demonstrates the feasibility of this is shown in FIG. 2 of the accompanying drawings in which known quantities of free dextran are added to inhibit the binding of anti-dextran RBC to dex-MFG. Here it is established that inhibition occurs with 500 ng of dextran but not at 50 ng (FIGS. 2d and 2e). By constructing a standard curve using data derived in this fashion one is able to quantitate the amount of antigen (or antibody) in a test sample.

The file of this patent contains at least one drawing executed in color. Copies of this patent with color drawing(s) will be provided by the Patent and Trademark Office upon request and payment of the necessary fee.

The invention also encompasses the use of antigen or antibody coupled MFG as a device for the separation by flotation of cells or molecules. In this instance, an antigen or antibody which specifically interacts with a complementary molecule on the surface of a cell or free in solution is coupled to MFG. Reaction of these MFG with a suspension of such cells or with a solution of such molecules will result in the flotation of the bound cells or molecules to the top of the tube. Molecules or cells thus separated, may be recovered from the MFG layer, unbound cells may be recovered from the cell pellet, and unbound molecules may be recovered from the underlying solution

What is claimed is:

1. A composition of matter for use in immunoassays and cell/molecular fractionation which comprises a buoyant matrix comprising milk fat globules which is surrounded by a lipid bilayer containing proteins and glycoproteins to which an antigen or an antibody is covalently coupled or incorporated.

2. A composition according to claim 1 in which the buoyant matrix is milk fat globules.

3. An immunoassay for the detection of an antibody which comprises contacting a sample suspected of containing an antibody with a solid floatable matrix comprising milk fat globules to which an antigen complementary to the suspected antibody is coupled; allowing time sufficient for an antigen-antibody complex to form if the test sample contains the suspected antibody; subsequently adding a visualizable indicator to which the antibody complementary to the antigen coupled to the maxtrix is attached; allowing time sufficient for an antigen-antibody complex to form between the antigen coupled to the matrix and the complementary antibody coupled to the indicator in the event that the test sample does not contain the antibody complementary to the antigen coupled to the matrix; and detecting the presence of the antibody by observing the position of the indicator system in a reaction tube, so that if antibody is present in the test sample, the color settles to the bottom, and if no antibody is present, the color rises to the top.

4. The immunoassay according to claim 3 wherein the test sample contains the suspected antibody and a complex is formed between the antibody contained in the test sample and the complementary antigen coupled to the matrix such that when the indicator with the complementary antibody coupled thereto is subsequently added it remains unbound as there is no unbound antigen coupled to the matrix and falls to the bottom forming a colored spot.

5. The immunoassay according to claim 3 wherein the test sample does not contain the suspected antibody and no complex is formed with the complementary antigen coupled to the matrix; such that when the indicator with the complementary antibody coupled thereto is added, a complex is formed between the antigen coupled to the matrix and the complementary antibody coupled to the indicator which then floats to the top resulting in a colored ring.

6. The immunoassay according to claim 3 wherein the color indicator is red blood cells, stained bacteria or enzymes.

7. An immunoassay for the detection of an antigen which comprises contacting a sample suspected of containing an antigen with a solid floatable matrix comprising milk fat globules to which an antibody complementary to the suspected antigen is coupled; allowing time sufficient for an antigen-antibody complex to form if the test sample contains the suspected antigen; subsequently adding a visualizable indicator to which the antigen complementary to the antibody coupled to the matrix is attached; allowing time sufficient for an antigen-antibody complex to form between the antibody coupled to the matrix and the complementary antigen coupled to the indicator in the event that the test sample does not contain the antigen complementary to the antibody coupled to the matrix; and detecting the presence of the antigen by observing the position of the indicator system in a reaction tube.

8. The immunoassay according to claim 7 wherein the test sample contains the suspected antigen and a complex is formed between the antigen contained in the test sample and the complementary antibody coupled to the matrix such that when the indicator with the complementary antigen coupled thereto is subsequently added it remains unbound, as there is no unbound antibody coupled to the matrix; and falls to the bottom forming a colored spot.

9. The immunoassay according to claim 7 wherein the test sample does not contain the suspected antigen and no complex is formed with the complementary antibody coupled to the matrix; such that when the indicator with the complementary antigen coupled thereto is added, a complex is formed between the antibody coupled to the matrix and the complementary antigen coupled to the indicator which then floats to the top resulting in a colored ring.

10. The immunoassay according to claim 7 wherein the indicator is red blood cells, stained bacteria or enzymes.

11. An immunoassay for the detection of an antibody which comprises contacting a sample suspected of containing an antibody with a solid floatable matrix comprising milk fat globules and a visualizable indicator to both of which a complementary antigen to the suspected antibody is coupled; allowing time sufficient for an antigen-antibody-antigen bridge complex to form if the test sample contains the suspected antibody, and detecting the presence of the antibody by observing the position of the indicator system in a reaction tube.

12. The immunoassay according to claim 11 wherein the test sample contains the suspected antibody and a bridge complex is formed between the antigen coupled to the matrix, the complementary antibody contained in the test sample and the antigen coupled to the indicator which then floats to the top resulting in a colored ring.

13. The immunoassay according to claim 11 wherein the test sample does not contain the suspected antibody and the complementary antigen coupled to the matrix remains unbound and floats to the top resulting in a white ring and the complementary antigen coupled to the indicator also remains unbound and falls to the bottom resulting in a colored spot.

14. The immunoassay according to claim 11 wherein the indicator is red blood cells, stained bacteria or enzymes.

15. An immunoassay for the detection of an antigen which comprises contacting a sample suspected of containing an antigen with a solid floatable matrix comprising milk fat globules and a visualizable indicator to both of which a complementary antibody to the suspected antigen is coupled; allowing time sufficient for an antibody-antigen- antibody bridge complex to form if the test sample contains the suspected antigen, and detecting the presence of the antigen by observing the position of the indicator system in a reaction tube.

16. The immunoassay according to claim 15 wherein the test sample contains the suspected antigen and a bridge complex is formed between the antibody coupled to the matrix, the complementary antigen contained in the test sample and the antibody coupled to the indicator which then floats to the top resulting in a colored ring.

17. The immunoassay according to claim 15 wherein the test sample does not contain the suspected antigen and the complementary antibody coupled to the matrix remains unbound and floats to the top resulting in a white ring and the complementary antibody coupled to the indicator also remains unbound and falls to the bottom resulting in a colored spot.

18. The immunoassay according to claim 15 wherein the color indicator consists of red blood cells, stained bacteria or enzymes.

19. A diagnostic kit for the detection of an antibody or antigen in a test sample, the kit being compartmentalized to receive:
   a. a first container containing a solid floatable matrix comprising milk fat globules to which is coupled the antigen or antibody complementary to the suspected antibody or antigen contained in the test sample, and;
   b. a second container containing a visualizable indicator to which is coupled the antibody or antigen complementary to the antigen or antibody bonded to the matrix.

20. The kit according to claim 19 wherein the indicator is red blood cells, stained bacteria or enzymes.

21. A diagnostic kit for the detection of an antibody or antigen in a test sample, the kit comprising a container containing a solid floatable matrix comprising milk fat globules and a visualizable indicator to both of which are coupled either the antigen complementary to the suspected antibody or the antibody complementary to the suspected antigen.

22. The kit according to claim 21 wherein the indicator is red blood cells, stained bacteria or enzymes.

23. A diagnostic kit according to claim 19 for the quantitative determination of the amount of antigen or antibody in a test sample, the kit having in addition containers containing serial two-fold dilutions of a known standard concentration of antigen or antibody for the generation of a standard curve such that these standard samples will be substituted for the test samples, so that an end point will be achieved whereby addition of most of the standard samples will result in a white ring, and addition of one or more of the more dilute standard will result in a red ring.

24. A diagnostic kit according to claim 21 for the quantitative determination of the amount of antigen or antibody in a test sample, the kit having in addition containers containing serial two-fold dilutions of a known standard concentration of antigen or antibody for the generation of a standard curve such that these standard samples will be substituted for the test samples, so that an end point will be achieved whereby addition of most of the standard samples will result in a red ring, and addition of one or more of the more dilute standard samples will result in a white ring.

25. A kit for the separation of cells or molecules, the kit comprising a container containing a solid floatable matrix comprising milk fat globules to which is coupled the antigen or antibody complementary to a surface molecule of the cell to be separated or to the molecule to be separated.

26. A kit for the separation of cells or molecules, the kit being compartmentalized to receive:
   a. a first container containing a solid floatable matrix comprising milk fat globules to which is coupled the antigen or antibody identical to a surface molecule of the cell to be separated or to a molecule to be separated,
   b. an antigen or antibody complementary to the antibody or antigen on the solid floatable matrix comprising milk fat globules and represented by the surface molecule to be separated or the molecule to be separated.

* * * * *